United States Patent [19]

Pilgram et al.

[11] 4,181,519
[45] Jan. 1, 1980

[54] DIPHENYLAMINE DERIVATIVE HERBICIDES

[75] Inventors: Kurt H. G. Pilgram; Richard D. Skiles, both of Modesto, Calif.

[73] Assignee: Shell Oil Company, Houston, Tex.

[21] Appl. No.: 5,633

[22] Filed: Jan. 22, 1979

Related U.S. Application Data

[63] Continuation-in-part of Ser. No. 876,593, Feb. 10, 1978, abandoned, which is a continuation-in-part of Ser. No. 761,515, Jan. 21, 1977, abandoned.

[51] Int. Cl.² .............. C07C 103/737; C07C 103/44; A01N 9/12; A01N 9/14
[52] U.S. Cl. ................................ 71/98; 71/103; 71/118; 260/557 R; 260/562 P
[58] Field of Search ............ 260/556 B, 557 R, 562 P; 71/98, 103, 118

[56] References Cited

U.S. PATENT DOCUMENTS

| | | | |
|---|---|---|---|
| 3,211,544 | 10/1965 | Dubrovin | 71/118 |
| 3,328,156 | 6/1967 | Hopkins | 71/118 |
| 3,407,056 | 10/1968 | Schwartz | 71/118 |
| 3,484,485 | 12/1969 | Schwartz | 260/557 R |
| 3,660,486 | 5/1972 | Thiele | 260/562 P |
| 3,753,679 | 8/1973 | Singhal | 71/98 |
| 4,090,865 | 5/1978 | Baker | 260/562 P X |

FOREIGN PATENT DOCUMENTS

| | | | |
|---|---|---|---|
| 749581 | 10/1970 | Belgium | 71/118 |
| 1921840 | 11/1969 | Fed. Rep. of Germany | 260/562 P |
| 1141183 | 1/1969 | United Kingdom | 260/557 R |
| 1246885 | 9/1971 | United Kingdom | 260/557 R |
| 1255161 | 12/1971 | United Kingdom | 260/557 R |
| 1344735 | 1/1974 | United Kingdom | 71/98 |

OTHER PUBLICATIONS

Martin et al., CA 74:12853w (1971).
Esso, CA 79:18343e (1973).

*Primary Examiner*—Thomas A. Waltz

[57] ABSTRACT

Compounds of the formula

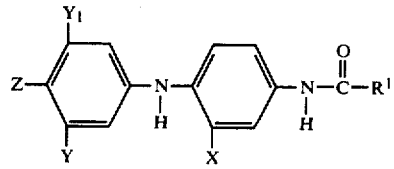

wherein X is halogen or (halo)alkyl; Y and $Y_1$ are hydrogen, halogen or (halo)alkyl; Z is hydrogen, halogen, (halo)alkyl, (halo)alkoxy, (halo)alkylthio, (halo)alkylsulfinyl, (halo)alkylsulfonyl or amino; with the proviso that at least one of Y, $Y_1$, and Z is other than hydrogen; and $R^1$ is alkyl or an optionally substituted cyclopropyl group, are useful as herbicides.

12 Claims, No Drawings

DIPHENYLAMINE DERIVATIVE HERBICIDES

CROSS-REFERENCE TO RELATED APPLICATIONS

This application is a continuation-in-part of Ser. No. 876,593 filed Feb. 10, 1978, now abandoned, which is a continuation-in-part of Ser. No. 761,515, filed Jan. 21, 1977, now abandoned.

BACKGROUND OF THE INVENTION

Field of the Invention

This invention relates to diphenylamine derivatives, their use as herbicides and to herbicidal compositions containing these diphenylamine derivatives.

SUMMARY OF THE INVENTION

The present invention is directed to a new class of compounds which are useful as herbicides to control undesirable plant growth. This class of compounds is characterized as amides derived from a carboxylic acid and certain diphenylamines.

DETAILED DESCRIPTION OF THE INVENTION

The present invention is directed to new compounds, particularly useful as herbicides, having the formula I

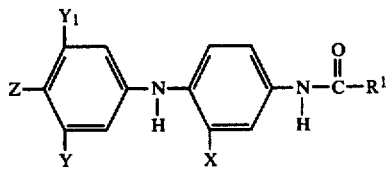

wherein

X is a halogen atom having an atomic number of from 9 to 35, inclusive, or an alkyl group containing from 1 to 6 carbon atoms optionally substituted by one or more halogen atoms;

Y and $Y_1$ each independently is a hydrogen atom, a halogen atom having an atomic number of from 9 to 35, inclusive or an alkyl or alkoxy group each optionally substituted by one or more halogen atoms;

Z is a hydrogen atom, a halogen atom having an atomic number of from 9 to 35, inclusive, an alkyl, alkoxy, alkylthio, alkylsulfinyl or alkylsulfonyl group in each of which the alkyl portion contains from 1 to 6 carbon atoms optionally substituted by one or more halogen atoms, or an amino group $R^2R^3N$ in which $R^2$ and $R^3$ each independently is a hydrogen atom or an alkyl group or cycloalkyl group of up to 6 carbon atoms and $R^3$ also can be an alkoxy group containing from 1 to 6 carbon atoms; and $R^1$ is an alkyl group containing from 1 to 4 carbon atoms or a cyclopropyl group of formula II

in which $R^4$ is a hydrogen atom, an alkyl group containing from 1 to 4 carbon atoms or a halogen atom having an atomic number of from 9 to 35, inclusive; with the proviso that when Z is a hydrogen atom then X is other than alkyl substituted by one or more halogen atoms and when $R^1$ is a group of formula II at least one of Y, $Y_1$ and Z is other than a hydrogen atom or when $R^1$ is alkyl then at least two of Y, $Y_1$ and Z is other than a hydrogen atom.

Examples of species contemplated within the scope of the invention include:

4'-(N,N-Dimethylamino)-2,3'-diethyl-4-(propionylamino)diphenylamine, 2,3',5'-Triethyl-4-(1-chlorocyclopropylcarbonylamino)diphenylamine, 4'-Methoxy-2,3'-dibromo-4-(acetylamino)diphenylamine, 4'-(Methylsulfonyl)-2-(trifluoromethyl)-4-(1-methylcyclopropylcarbonylamino)diphenylamine, 4'-Bromo-2,3'-dichloro-4-(1-methylcyclopropylcarbonylamino)diphenylamine, 4'-Chloro-2-(trifluoromethyl)-4-(acetylamino)diphenylamine, 2,4'-Bis(trifluoromethyl)-4-(cyclopropylcarbonylamino)diphenylamine, 4'-Isopropoxy-2,3'-bis(trifluoromethyl)-4-(1-methylcyclopropylcarbonylamino)diphenylamine, 4'-Isopropylamino-2,3'-bis(trifluoromethyl)-4-(acetylamino)diphenylamine, 4'-(1-Cyclopropylethoxy)-2,3'-bis(trifluoromethyl)-4-(cyclopropylcarbonylamino)diphenylamine, 2,3',4',5'-Tetrachloro-4-(1-methylcyclopropylcarbonylamino)diphenylamine, 2,3',4',5'-Tetrakis(trifluoromethyl)-4-(acetylamino)-diphenylamine, 4'-(Ethylsulfinyl)-2,3'-bis(trifluoromethyl)-4-(cyclopropylcarbonylamino)diphenylamine.

The compounds of formula I are acylamino derivatives of diphenylamines. The acyl groups, $R^1$, is derived from certain carboxylic acids. The group $R^1$ is an alkyl group containing from 1 to 4 carbon atoms or a cyclopropyl group of the formula II

in which $R^4$ is a hydrogen atom, an alkyl group containing from 1 to 4 carbon atoms or a halogen atom having an atomic number of from 9 to 35, inclusive. For example, R' is methyl, ethyl, isopropyl, tert-butyl and the like or a cyclopropyl group of formula II in which $R^4$ is a hydrogen atom or a methyl group.

Preferred because of their herbicidal properties are those compounds wherein $R^1$ is a cyclopropyl group of formula II in which $R^4$ is a hydrogen atom or a methyl group.

The group X can be, for example, chlorine, bromine, fluorine, methyl, ethyl, n-propyl, trifluoromethyl or the like.

Preferred because of their herbicidal properties are those compounds of formula I in which X is chlorine, bromine, methyl or trifluoromethyl. Especially suitable are those compounds in which X is trifluoromethyl.

The groups Y and $Y_1$ independently can be hydrogen, chlorine, bromine, fluorine, methyl, ethyl, n-propyl, trifluoromethyl or the like.

Preferred because of their herbicidal properties are those compounds of formula I in which Y and $Y_1$ each independently is chlorine, bromine, methyl, trifluoromethyl or hydrogen. Especially suitable are those compounds wherein Y is one of the above named groups and $Y_1$ is hydrogen.

The group Z can be hydrogen, chlorine, bromine, fluorine, unsubstituted amino, methylamino, dimethylamino, isopropylamino, methoxymethylamino, tert-butylamino, 2-chloroethoxy, isopropoxy, 1-cyclopropylethoxy, trifluoromethoxy, methyl, ethyl, tert-butyl, methylthio, methylsulfonyl, trifluoromethylsulfonyl, ethylsulfinyl, isopropylsulfinyl, isopropylthio, isopropylsulfonyl, and the like.

One preferred subclass of the invention because of their herbicidal properties includes those compounds of the invention wherein Z is halogen, especially chlorine or fluorine.

The diphenylamine derivatives of the invention can be prepared by treating, in the presence of a base, an anilide containing the appropriate Y, $Y_1$ and Z substituents with a 4-chloronitrobenzene further substituted by the desired X substituent at the 3-position, reducing the resulting 4-nitrodiphenylamine and acylating the resulting aminodiphenylamine with the appropriate carboxylic acid halide to introduce the desired substituent $R^1$.

Reactions for preparing the 4-nitrodiphenylamine are described, for example, in Rondestvedt, Jr., C.S., *J. Org. Chem.*, 42 (10) pages 1786–90 (1977). When anilides other than formanilide are used, it is necessary to hydrolyze the initial reaction product to the 4-nitrodiphenylamine.

The reduction of the 4-nitrodiphenylamine is readily carried out in boiling water containing iron filings and up to 5% of acetic or hydrochloric acid. However, any of numerous reduction techniques that reduce an aromatic nitro group to amino are applicable here (see R. Schröter and F. Möller in Methoden der Organische Chemie. "Houben-Weyl", Vol. 11, 1, part IV, p. 341–731, Georg Thieme Verlag, Stuttgart (1957)).

The acylation reaction is conducted by treating the 4-aminodiphenylamine derivative with a carboxylic acid halide, e.g., chloride, in a suitable solvent such as ether, tetrahydrofuran, benzene, toluene or hexane in the presence of one molar equivalent of an organic or inorganic base that can serve as acceptor for the hydrogen chloride formed in the reaction. Organic bases such as tertiary amines (pyridine, triethylamine, collidine, N,N-dimethylaniline, ethyldiisopropylamine) or inorganic bases ($Na_2CO_3$, $NaHCO_3$, $K_2CO_3$, $CaCO_3$) may be used to trap the hydrogen chloride formed during acylation.

The cycloalkylcarboxylic chlorides used in the reaction or simple esters from which they can be generated are generally known in the art as for example in U.S. Pat. No. 3,277,171, 3,211,544, 3,484,485 and South African application No. 64/1283. The 1-fluorocycloalkylcarboxylic chlorides can be readily prepared by treating 1-chlorocycloalkylcarboxylic acid ethyl ester with potassium fluoride at elevated temperatures optionally in the presence of solvents and/or phase transfer catalysts and converting the ester to the acid chloride in a known manner. The 1-bromocycloalkylcarboxylic chlorides can be prepared by bromination of cycloalkylcarboxylic chlorides under refluxing conditions in a nitrogen atmosphere.

The compounds of the invention have been found to be useful for controlling undesirable plant growth. That is, certain members of the class have been found to be herbicially effective against a wide range of plant species, particularly for post-emergence treatment. Others of the class are effective only against a limited number of plant species and are considered to be selective herbicides. Some of the compounds exhibit a high degree of herbicidal activity in the control of a variety of economically important species of grasses and broad-leaved weeds. Some of the compounds are particularly useful as selective herbicides for use in certain important crops.

The invention includes plant growth regulating compositions comprising a carrier or a surface-active agent, or both a carrier and a surface-active agent, and, as active ingredient, at least one compound of formula I. Likewise the invention also includes a method of controlling undesirable plant growth which comprises applying to the locus an effective amount of a compound of Formula I.

The term "carrier" as used herein means a solid or fluid material, which may be inorganic or organic and of synthetic or natural origin, with which the active compound is mixed or formulated to facilitate its application to the plant, seed, soil or other object to be treated, or its storage, transport or handling.

Suitable solid carriers are natural and synthetic clays and silicates, for example, natural silicas such as diatomaceous earths; magnesium silicates, for example, attapulgites and vermiculites; aluminum silicates, for example, kaolinites, montmorillinites and micas; calcium carbonates; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; solid polychlorophenols; bitumen, waxes such as, for example, beeswax, paraffin wax, and chlorinated mineral waxes; and solid fertilizers, for example, superphosphates.

Examples of suitable fluid carriers are water, alcohols such as, for example, isopropanol, glycols; ketones such as, for example, acetone, methyl ethyl ketone, methyl isobutyl ketone and cyclohexanone; ethers; aromatic hydrocarbons such as, for example, benzene, toluene and xylene; petroleum fractions such as, for example, kerosene, light mineral oils; chlorinated hydrocarbons such as, for example, carbon tetrachloride, perchloroethylene, trichloroethane, including liquified normally vaporous gaseous compounds. Mixtures of different liquids are often suitable.

The surface active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated caster oil, and sodium alkylaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates and aerosols. Wettable powders are usually compounded to contain 25, 50 or 75% weight of toxicant and usually contain in addition to solid carrier, 3–10% weight of a dispersing agent, 1–5% weight of a surface-active agent and where necessary, 0–10% by weight of stabilizer(s) and/or other additives such as penetrant or stickers. Dusts are usually formulated as a dust concentrate having a similar composition to that of a wettable powder but without a dispersant or surface-active agent, and are diluted in the field with further solid carrier to give a composition usually containing ½–10% weight of toxicant. Granules are usually prepared to have a size between 10 and 100 BS mesh (1.676–0.152 mm), and may be manufactured by agglomeration or impregnation techniques. Generally granules will contain ½–25% weight toxicant and 0–10% weight of additives such a stabilizers, slow release modifiers and binding agents. Emulsifiable concentrates usually contain, in addition to the solvent and, when necessary, co-solvent, 10–50% weight per volume toxicant, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight toxicant, 0.5–5% weight of dispersing agents, 1–5% weight of surface-active agent, 0.1–10% weight of suspending agents such as protective colloids and thixotropic agents, 0–10% weight of appropriate additives such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick mayonnaise-like consistency.

The compositions of the invention may also contain other ingredients, for example, other compounds possessing pesticidal, especially insecticidal, acaricidal, herbicidal or fungicidal, properties.

The method of applying the compounds of this invention comprises applying a compound of Formula I, ordinarily in a composition of one of the aforementioned types, to a locus or area to be protected from undesirable plant growth. The active compound, of course, is applied in amounts sufficient to exert the desired action.

The amount of compound of the invention to be used in controlling undesirable vegetation will naturally depend on the condition of the vegetation, the degree of activity desired, the formulation used, the mode of application, the climate, the season of the year, and other variables. Recommendations as to precise amounts are, therefore, not possible. In general, however, application to the locus to be protected of from 0.1 to 10.0 pounds per acre of the compound used in this invention will be satisfactory.

EXAMPLES

The manner in which the compounds of this invention can be prepared is illustrated in the following examples, which demonstrate the preparation of typical species of the invention. In these examples, the identies of all compounds, intermediates and final, were confirmed by elemental analysis, and infrared and nuclear magnetic spectral analyses. The examples are for the purpose of illustration only and should not be regarded as limiting the invention in any way.

EXAMPLE 1

2,3'-Bis(trifluoromethyl)-4'-chloro-4-(1-methylcyclopropylcarbonylamino)diphenylamine (a) 4-Chloro-3-(trifluoromethyl)formanilide A mixture containing 97.8 g of 4-chloro-3-(trifluoromethyl)aniline and 405 ml of 98% formic acid was stirred and refluxed at about 106° C. for 3 hours. The resulting mixture was poured over ice water and filtered. The filter cake was washed with water and dried to yield 109.5 g (98%) of colorless product, mp 102°–104° C.

(b) 2,3'-Bis(trifluoromethyl)-4'-chloro-4-nitrodiphenylamine

To a stirred solution of 109 g of (a) above in 300 ml of dimethylformamide was added portionwise 25.8 g of 50% sodium hydride in mineral oil. The internal temperature was controlled at or below 30° C. by external cooling with an ice bath. After completion of this addition, the mixture was stirred and heated at 90° C. for 10 minutes. To the cooled (25° C.) mixture was added 110.1 g. of 2-chloro-4-nitrobenzotrifluoride. The reaction mixture which became dark red in color was heated gradually. At about 110° C., an exothermic reaction accompanied by the evolution of carbon monoxide gas was observed and cooling was necessary. When the exothermic reaction had subsided, the mixture was stirred and refluxed at 156° C. for 2.5 hours, cooled, diluted with 1.5 l of ice water and extracted with 3×400 ml of ether. The combined ether extracts were washed with 500 ml of water, dried over anhydrous magnesium sulfate, and concentrated to dryness. The residual dark syrup, 195 g, was purified by silica chromatography to yield 86.5 g (46%) of yellow product; mp 126°–130° C.

(c) 4-Amino-2,3'-bis(trifluoromethyl)-4'-chlorodiphenylamine

A solution containing 80 g of (b) above in 250 ml of tetrahydrofuran was hydrogenated in a Parr shaker at 60 psi hydrogen pressure at ambient temperature for 4 hours in the presence of 3 g of Raney-nickel. The reaction mixture was filtered and the filtrate was concentrated under reduced pressure. The residual light yellow oil crystallized from hexane to yield 73 g (98%) of product; mp 80°–83° C.

(d) 2,3'-Bis(trifluoromethyl)-4'-chloro-4-(1-methylcyclopropylcarbonylamino)diphenylamine To a solution containing 17.8 g of (c) above and 5.0 g of triethylamine in 100 ml of tetrahydrofuran was added dropwise at ambient temperature 6.0 g of 1-methylcyclopropanecarbonyl chloride. This addition was exothermic to 45° C. The reaction mixture was refluxed (70° C.) for one hour, poured over ice water and extracted with 3×150 ml of ether. The combined extracts were dried (MgSO₄) and concentrated to dryness. The residual light yellow syrup, 21.6 g, was purified by silica chromatography to yield 19 g (87%) of the desired product as a viscous liquid.

EXAMPLE 2

2,3′,4′-Trichloro-4-(1-methylcyclopropylcarbonylamino)diphenylamine (a) 3,4-Dichloroformanilide A mixture containing 81 g of 3,4-dichloroaniline in 405 ml of 90% formic acid was stirred and refluxed (106° C.) for about 2 hours. The hot mixture was poured over ice water and filtered, and the solid product was washed with water and dried to yield 92.8 g (98%) of white solid; mp 108°–111° C.

(b) 4-Nitro-2,3′,4′-trichloro-diphenylamine

A warm mixture of 92.8 g of (a) above and 150 ml of toluene was added dropwise to a stirred suspension containing 11.2 g of metallic sodium in 100 ml of refluxing toluene. The rate of addition was adjusted so that reflux could be controlled. After ten minutes, 93.7 g of 3,4-dichloronitrobenzene was added to the reaction mixture, followed by 100 ml of dimethylformamide. Removal of 200 ml of toluene by distillation caused the internal temperature to rise to 160° C. The reaction mixture was stirred at this temperature for 2 hours. After the dropwise addition of 30 g of sodium hydroxide in 200 ml of water, the reaction mixture was steam distilled until the distillate was homogenous. After the addition of 200 ml of water, the reaction mixture was cooled and filtered to yield 128.6 g (83%) of the desired product; mp 150° C. and 169°–170° C. from glacial acetic acid.

(c) 4-Amino-2,3′,4′-trichloro-diphenylamine

A mixture containing 31.7 g of (b) above and 3 g of Raney-nickel in 250 ml of tetrahydrofuran was hydrogenated for 2.5 hours in a Parr shaker at 50–60 psi of hydrogen gas. The reaction mixture was filtered through Celite and the filtrate was concentrated under reduced pressure to yield 28.5 g (99%) of the desired product as a dark syrup. Thin-layer chromatography indicated the presence of a single compound.

(d) 2,3′,4′-Trichloro-4-(1-methylcyclopropylcarbonylamino)diphenylamine

To a stirred solution containing 7.2 g of (c) above and 2.5 g of triethylamine in 75 ml of tetrahydrofuran was added dropwise within a period of two minutes 3.0 g of 1-methylcyclopropanecarbonyl chloride. The resulting reaction was exothermic, causing the internal temperature to rise to 50° C. The mixture was stirred and heated at 70° C. for one hour, concentrated under reduced pressure, diluted with 300 ml of water and extracted with 3×150 ml portions of ether. The combined ether extracts were concentrated. The residual syrup was purified by silica chromatography to yield 4.0 g (43%) of the desired product as a colorless solid; mp 109°–111° C.

EXAMPLES 3–37

Using synthesis procedures similar to those of Examples 1 and 2 above, additional diphenylamine derivatives of the invention were prepared as set forth in Table I below:

Table I

| Example | X | Y | $Y_1$ | Z | $R^1$ | % Yield | Mp, °C. |
|---|---|---|---|---|---|---|---|
| 3 | Cl | Cl | H | Cl | △ | 64 | 154–6 |
| 4 | Cl | Cl | H | Cl | —C(CH₃)₃ | 40 | 121–4 |
| 5 | Cl | Cl | H | Cl | —CH₃ | 37 | 134–7 |
| 6 | Cl | Cl | H | Cl | —C₂H₅ | 58 | 126–9 |
| 7 | Cl | Cl | H | Cl | —CH(CH₃)₂ | 45 | 126–8 |
| 8 | CF₃ | Cl | H | Cl | △ | | |
| 9 | CF₃ | Cl | H | Cl | △–CH₃ | 89 | 106–9 |
| 10 | CF₃ | H | H | Cl | —CH₃ | 96 | 140–3 |
| 11 | CF₃ | H | H | Cl | △ | 73 | 146–9 |
| 12 | CF₃ | H | H | Cl | △–CH₃ | 99 | oil |
| 13 | CF₃ | Cl | H | F | —CH₃ | 62 | oil |
| 14 | CF₃ | Cl | H | F | △ | 46 | oil |
| 15 | CF₃ | Cl | H | F | △–CH₃ | 56 | oil |

Table I-continued
DIPHENYLAMINE DERIVATIVES
| Example | X | Y | Y₁ | Z | R¹ | % Yield | Mp, °C. |
|---|---|---|---|---|---|---|---|
| 16 | CF₃ | Cl | H | Br |  | 93 | 132–3 |
| 17 | CF₃ | Cl | H | Br |  | 89 | 118–20 |
| 18 | CF₃ | CF₃ | H | Cl | —CH₃ | 90 | oil |
| 19 | CF₃ | CF₃ | H | Cl |  | 85 | 168–70 |
| 20 | CF₃ | CH₃ | H | F | —CH₃ | 97 | oil |
| 21 | CF₃ | CF₃ | H | F |  | 97 | 124–7 |
| 22 | CF₃ | CF₃ | H | F |  | 99 | oil |
| 23 | Cl | CF₃ | CF₃ | H |  | 95 | 179–81 |
| 24 | Cl | CF₃ | CF₃ | H |  | 91 | 165–7 |
| 25 | Cl | Cl | Cl | H |  | | 152–5 |
| 26 | Cl | Cl | Cl | H |  | 71 | 205–7 |
| 27 | CF₃ | Cl | Cl | H |  | 94 | 136–8 |
| 28 | CF₃ | Cl | Cl | H |  | 88 | 148–50 |
| 29 | CF₃ | CH₃ | H | CH₃ |  | 83 | 176–9 |
| 30 | CF₃ | CH₃ | H | CH₃ |  | 81 | 138–41 |
| 31 | CF₃ | CF₃ | H | i-C₃H₇O | —CH₃ | 94 | oil |
| 32 | CF₃ | CF₃ | H | i-C₃H₇O |  | 81 | 110–2 |
| 33 | CF₃ | CH₃O | CH₃O | H |  | 98 | 125–7 |
| 34 | CF₃ | CH₃O | CH₃O | H |  | 95 | 90–3 |
| 35 | CF₃ | CF₃ | H | i-C₃H₇NH |  | 91 | 109–10 |
| 36 | CF₃ | CF₃ | H | i-C₃H₇O |  | 96 | 66–8 |

Table I-continued

DIPHENYLAMINE DERIVATIVES

| Example | X | Y | Y₁ | Z | R¹ | % Yield | Mp, °C. |
|---|---|---|---|---|---|---|---|
| 37 | CF₃ | F | H | F |  CH₃ | 99 | oil |

EXAMPLE OF HERBICIDAL ACTIVITY

The post-emergence activity of the compound of this invention was evaluated by spraying 7 to 13-day old weed seedlings to runoff with a liquid formulation of the test compounds at the rates of 250 (Rate I) and 2500 ppm (Rate II). The sprayed plants were held under controlled conditions for 8 to 9 days and the effect of the test compound was then evaluated visually, the results being rated on a scale of 0 to 9 (0=no control, 9=complete control or death of seedlings).

The results of the post-emergence tests are summarized in Table II.

Table II

RESULTS OF THE HERBICIDE ACTIVITY SCREEN

Post-Emergence (Foliar)

| Example | Crabgrass I | Crabgrass II | Pigweed I | Pigweed II | Downy Brome I | Downy Brome II | Sicklepod I | Sicklepod II | Velvet Leaf I | Velvet Leaf II |
|---|---|---|---|---|---|---|---|---|---|---|
| 1 | 9 | 9 | 9 | 9 | 3 | 5 | 9 | 9 | 8 | 9 |
| 2 | 6 | 8 | 8 | 9 | 6 | 7 | 8 | 9 | 0 | 5 |
| 3 | 6 | 7 | 8 | 9 | 6 | 7 | 0 | 9 | 7 | 7 |
| 4 | 5 | 6 | 9 | 9 | 8 | 8 | 6 | 8 | 2 | 3 |
| 5 | 7 | 9 | 0 | 9 | 5 | 7 | 7 | 8 | 5 | 7 |
| 6 | 3 | 6 | 4 | 9 | 3 | 6 | 5 | 7 | 5 | 9 |
| 7 | 2 | 3 | 8 | 8 | 2 | 5 | 5 | 9 | 4 | 6 |
| 8 | 9 | 9 | 9 | 9 | 8 | 9 | 7 | 9 | 7 | 9 |
| 9 | 9 | 9 | 9 | 9 | — | — | 7 | 9 | 8 | 8 |
| 10 | 0 | 4 | 3 | 6 | 0 | 0 | 3 | 7 | 0 | 2 |
| 11 | 7 | 7 | 8 | 9 | 2 | 4 | 7 | 8 | 3 | 6 |
| 12 | 8 | 8 | 9 | 9 | 4 | 7 | 7 | 9 | 6 | 8 |
| 13 | 0 | 8 | 2 | 9 | 2 | 2 | 3 | 4 | 2 | 2 |
| 14 | 8 | 9 | 9 | 9 | 3 | 9 | 5 | 9 | 7 | 9 |
| 15 | 7 | 9 | 9 | 9 | 7 | 9 | 8 | 9 | 9 | 9 |
| 16 | 8 | 8 | 8 | 8 | 9 | 9 | 8 | 9 | 4 | 7 |
| 17 | 7 | 9 | 9 | 9 | 6 |   | 7 | 8 | 8 | 9 |
| 18 | 0 | 2 | 4 | 8 | 0 | 3 | 4 | 7 | 2 | 5 |
| 19 | 6 | 7 | 8 | 9 | 3 | 3 | 7 | 9 | 5 | 6 |
| 20 | 0 | 4 | 3 | 8 | 2 | 3 | 0 | 7 | 0 | 2 |
| 21 | 3 | 4 | 7 | 9 | 2 | 3 | 5 | 7 | 0 | 7 |
| 22 | 4 | 6 | 9 | 9 | 2 | 5 | 7 | 9 | 7 | 7 |
| 23 | 0 | 3 | 0 | 9 | — | 6 | 3 | 7 | 0 | 6 |
| 24 | 0 | 0 | 0 | 9 | — | — | 3 | 8 | 7 | 7 |
| 25 | 7 | 9 | 9 | 9 | 7 | 9 | 8 | 8 | 8 | 9 |
| 26 | 7 | 8 | 7 | 9 | 4 | 7 | 4 | 8 | 7 | 9 |
| 27 | 6 | 7 | 3 | 9 | 3 | 9 | 3 | 7 | 6 | 4 |
| 28 | 4 | 8 | 8 | 9 | 4 | 9 | 4 | 9 | 5 | 9 |
| 29 | 6 | 9 | 7 | 9 | 6 | 9 | 7 | 9 | 8 | 9 |
| 30 | 8 | 9 | 9 | 9 | 9 | 9 | 9 | 9 | 8 | 9 |
| 31 | 2 | 8 | 6 | 8 | 2 | 4 | 4 | 6 | 2 | 8 |
| 32 | 7 | 7 | 8 | 9 | 2 | 6 | 5 | 9 | 3 | 3 |
| 33 | 3 | 9 | 8 | 9 | 3 | 8 | 6 | 8 | 8 | 9 |
| 34 | 2 | 8 | 7 | 9 | 3 | 7 | 7 | 8 | 6 | 9 |
| 35 | 0 | 4 | 2 | 8 | 0 | 3 | 0 | 3 | 0 | 3 |
| 36 | 3 | 6 | 5 | 8 | 3 | 3 | 3 | 7 | 0 | 5 |

I claim:

1. A compound of the formula

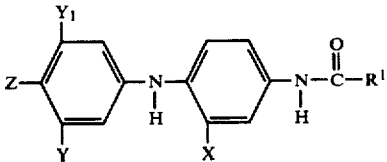

wherein
X is a halogen atom having an atomic number of from 9 to 35, inclusive, or an alkyl group containing from 1 to 6 carbon atoms optionally substituted by one or more halogen atoms;

Y and Y₁ each independently is a hydrogen atom, a halogen atom having an atomic number of from 9 to 35, inclusive, or an alkyl or alkoxy group each optionally substituted by one or more halogen atoms;

Z is a hydrogen atom, a halogen atom having an atomic number of from 9 to 35, inclusive, an alkyl, alkoxy, alkylthio, alkylsulfinyl or alkylsulfonyl group in each of which the alkyl portion contains from 1 to 6 carbon atoms optionally substituted by one or more halogen atoms, or an amino group R²R³N in which R² and R³ each independently is a hydrogen atom or an alkyl or cycloalkyl group containing up to 6 carbon atoms or R³ can also be an alkoxy group containing from 1 to 6 carbon atoms;

R¹ is an alkyl group containing from 1 to 4 carbon atoms, or a cyclopropyl group of formula II

(II)

in which R⁴ is a hydrogen atom or an alkyl group containing from 1 to 4 carbon atoms or a halogen atom having an atomic number of from 9 to 35, inclusive; with the proviso that when Z is a hydrogen atom then X is other than an alkyl group substituted by one or more halogen atoms and when R¹ is a group of formula II then at least one of Y, Y¹ and Z is other than a hydrogen atom or when R¹ is alkyl then at least two of Y, Y¹ and Z is other than a hydrogen atom.

2. A compound according to claim 1 wherein R¹ is a cyclopropyl group of formula II in which R⁴ is a hydrogen atom or a methyl group.

3. A compound according to claim 2 wherein Y₁ is a hydrogen atom.

4. A compound according to claim 3 wherein X is a trifluoromethyl group, chlorine, bromine or a methyl group.

5. A compound according to claim 4 wherein Y is a trifluoromethyl group or chlorine and Z is chlorine, fluorine, bromine or a trifluoromethyl group.

6. A compound according to claim 5 wherein X is a trifluoromethyl group.

7. A compound according to claim 6 wherein Z is chlorine, fluorine, bromine or a trifluoromethyl group.

8. A compound according to claim 7 wherein Y is chlorine and Z is fluorine.

9. A compound according to claim 7 wherein Z is chlorine.

10. A compound according to claim 1 wherein $R^4$ is a hydrogen atom or a methyl group; $Y_1$ is a hydrogen atom; and X and Y each independently is a trifluoromethyl group, chlorine, bromine or fluorine.

11. A herbicidal composition comprising a herbicidally effective amount of a compound according to claim 1 and at least one surface-active agent or carrier.

12. A method for controlling undesirable plant growth at a locus to be protected which comprises applying to the locus to be protected a herbicidally effective amount of a compound according to claim 1.

* * * * *